United States Patent
Suzuki

(10) Patent No.: US 9,163,106 B2
(45) Date of Patent: Oct. 20, 2015

(54) LIQUID RESOL-TYPE PHENOLIC RESIN AND WET PAPER FRICTION MATERIAL

(71) Applicant: SUMITOMO BAKELITE CO., LTD., Tokyo (JP)

(72) Inventor: Yuji Suzuki, Tokyo (JP)

(73) Assignee: SUMITOMO BAKELITE CO., LTD., Tokyo (JP)

( * ) Notice: Subject to any disclaimer, the term of this patent is extended or adjusted under 35 U.S.C. 154(b) by 0 days.

(21) Appl. No.: 14/391,256

(22) PCT Filed: May 29, 2013

(86) PCT No.: PCT/JP2013/003385
§ 371 (c)(1),
(2) Date: Oct. 8, 2014

(87) PCT Pub. No.: WO2013/179660
PCT Pub. Date: Dec. 5, 2013

(65) Prior Publication Data
US 2015/0065756 A1    Mar. 5, 2015

(30) Foreign Application Priority Data

May 31, 2012    (JP) ................. 2012-123992

(51) Int. Cl.
| | | |
|---|---|---|
| C08G 14/04 | (2006.01) | |
| C08G 8/20 | (2006.01) | |
| C08G 10/02 | (2006.01) | |
| F16D 69/02 | (2006.01) | |
| C07C 39/18 | (2006.01) | |
| C08G 8/08 | (2006.01) | |

(52) U.S. Cl.
CPC ............... *C08G 10/02* (2013.01); *C07C 39/18* (2013.01); *C08G 8/08* (2013.01); *C08G 8/20* (2013.01); *C08G 14/04* (2013.01); *F16D 69/026* (2013.01)

(58) Field of Classification Search
CPC .................................. C08G 14/04; C08G 8/20
USPC .................. 528/155, 129, 230; 525/480, 507
See application file for complete search history.

(56) References Cited

U.S. PATENT DOCUMENTS 6,579,963 B1    6/2003    Vergopoulou-Markessini et al.

FOREIGN PATENT DOCUMENTS

| JP | 48-29530 | 9/1973 |
| JP | 5-279496 A | 10/1993 |
| JP | 9-59599 A | 3/1997 |
| JP | 2002-527587 A | 8/2002 |
| JP | 2008-189749 A | 8/2008 |
| JP | 2008-255133 A | 10/2008 |

OTHER PUBLICATIONS

International Search Report dated Jul. 2, 2013, issued in corresponding application No. PCT/JP2013/003385.

*Primary Examiner* — Elvis O Price
(74) *Attorney, Agent, or Firm* — Westerman, Hattori, Daniels & Adrian, LLP

(57) ABSTRACT

A straight-chain unsaturated hydrocarbon group having equal to or more than 10 carbon atoms is bonded to at least one or more of meta positions of all of phenol structure units.

9 Claims, No Drawings

LIQUID RESOL-TYPE PHENOLIC RESIN AND WET PAPER FRICTION MATERIAL

TECHNICAL FIELD

The present invention relates to a liquid resol-type phenolic resin and a wet paper friction material.

BACKGROUND ART

A phenolic resin which is a thermosetting resin is mainly and widely used as a binder that bonds materials which become base materials of a molded product. Since the phenolic resin is excellent in mechanical characteristics, electrical characteristics, or adherence, it is used in various fields. Particularly, in recent years, the amount used of a friction material in which the phenolic resin is used as the binder in vehicles, railway vehicles, or the like has increased.

Among these, a liquid resol-type phenolic resin is generally used in a friction material which is called a wet paper friction material and is used in an automatic change gear or the like of an automatic vehicle or the like. The required characteristics with respect to phenolic resin for the wet paper friction material have increased year by year. Particularly, in order to improve the friction characteristics, demand for improving flexibility of the phenolic resin has increased. However, a general cured material of a phenolic resin has a property of being excellent in mechanical properties, but since it is firm and fragile, it cannot be said that the general cured material thereof is excellent in flexibility.

As a method of solving the above-described problem, an attempt of improving the flexibility using drying oil or the like has been examined as a modifier in a reaction while synthesizing the phenolic resin (for example, Patent Document 1). Such a drying oil-modified phenolic resin to which a flexible aliphatic hydrocarbon group is introduced has a characteristic of high flexibility compared to an unmodified phenolic resin.

RELATED DOCUMENT

Patent Document

[Patent Document 1] Japanese Unexamined Patent Publication No. 9-59599

DISCLOSURE OF THE INVENTION

However, in the drying oil-modified phenolic resin disclosed in Patent Document 1, there is a disadvantage that the effect of improving the flexibility is insufficient because all of aliphatic hydrocarbon groups are not bonded to phenol structure units. In addition, in a case where the aliphatic hydrocarbon group is bonded to a cross-linking point in the phenol structure units, a reaction point of the phenolic resin reduces, and therefore, there is a disadvantage that hardenability deteriorates.

In addition, in recent years, a further improvement of friction characteristics has been expected in addition to an improvement of fuel consumption of a vehicle or an improvement of a burden on a friction material. For this reason, an improvement of the flexibility has been expected for the phenolic resin for the friction material.

The present invention has been made in consideration of the circumstances, and an object of the invention is to provide a liquid resol-type phenolic resin through which it is possible to obtain a wet paper friction material which is excellent from the viewpoint of hardenability as a characteristic of the phenolic resin and is more excellent in flexibility, and the wet paper friction material formed using the same.

The present inventor has completed the present invention by conducting extensive studies based on a substituent existing in the phenol structure units in order to provide a liquid resol-type phenolic resin which has a characteristic excellent from the viewpoint of hardenability and through which it is possible to obtain a wet paper friction material excellent in flexibility. As a result, it was found that it is effective to set the phenolic resin in which a straight-chain unsaturated hydrocarbon group having equal to or more than 10 carbon atoms is bonded to at least one or more of meta positions of all of the phenol structure units.

According to the present invention, the liquid resol-type phenolic resin, in which a straight-chain unsaturated hydrocarbon group having equal to or more than 10 carbon atoms is bonded to at least one or more of meta positions of all of the phenol structure units, is provided.

Furthermore, according to the present invention, a wet paper friction material formed using the above-described liquid resol-type phenolic resin is provided.

According to the invention, it is possible to provide a liquid resol-type phenolic resin which is excellent from the viewpoint of hardenability as a characteristic of the phenolic resin and through which it is possible to obtain a wet paper friction material excellent in flexibility, and the wet paper friction material using the same.

DESCRIPTION OF EMBODIMENTS

Hereinafter, the liquid resol-type phenolic resin and the wet paper friction material according to the present embodiment will be described in detail.

<Liquid Resol-Type Phenolic Resin>

The liquid resol-type phenolic resin according to the present embodiment is characterized in that a straight-chain unsaturated hydrocarbon group having equal to or more than 10 carbon atoms is bonded to at least one or more of meta positions of all of phenol structure units. In this manner, it is possible to obtain a liquid resol-type phenolic resin which is excellent from the viewpoint of hardenability as a characteristic of the phenolic resin and is suitable for obtaining a wet paper friction material excellent in flexibility.

In the liquid resol-type phenolic resin according to the present embodiment, the phenol structure unit means a structural unit having at least a structure in which a direct hydroxyl group (—OH) is bonded to a carbon of a benzene ring.

In addition, it is preferable that the liquid resol-type phenolic resin according to the present embodiment be obtained through a reaction with phenols (A) in which a straight-chain unsaturated hydrocarbon group having equal to or more than 10 carbon atoms is bonded to at least one or more of meta positions. By doing this, it is possible to obtain a liquid resol-type phenolic resin which is suitable for obtaining a wet paper friction material more excellent in flexibility.

It is preferable that the phenols (A) according to the present embodiment include a structure represented by the following general formula (1).

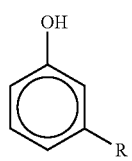

(1)

(In the formula, R represents a straight-chain unsaturated hydrocarbon group having equal to or more than 10 carbon atoms. However, a hydrogen atom which is bonded to a benzene ring having a phenolic hydroxyl group may be substituted by a substituent.)

In addition, the substituent that substitutes the hydrogen atom which is bonded to the benzene ring having the phenolic hydroxyl group is not particularly limited, but examples thereof include an acetyl group, a methyl group, or the like.

In addition, the straight-chain unsaturated hydrocarbon group, which is bonded to at least one or more of meta positions of all of the phenol structure units, preferably has equal to or more than 10 carbon atoms, and more preferably has equal to or more than 12 carbon atoms. In contrast, the straight-chain unsaturated hydrocarbon group, which is bonded to at least one or more of meta positions of all of the phenol structure units, preferably has equal to or less than 20 carbon atoms, and more preferably has equal to or less than 18 carbon atoms. By doing this, it is possible to obtain the liquid resol-type phenolic resin which is excellent from the viewpoint of hardenability as a characteristic of the phenolic resin and is suitable for obtaining the wet paper friction material more excellent in flexibility. If the number of carbon atoms of the straight-chain unsaturated hydrocarbon group is too large, it is difficult to dilute the resin using an organic agent during impregnation. In contrast, if the number of carbon atoms of the straight-chain unsaturated hydrocarbon group is too small, it is difficult to improve the flexibility.

In addition, the phenols (A) according to the present embodiment are not particularly limited, but examples thereof include 3-dodecenyl phenol; 3-tridecenyl phenol; 3-pentadecenyl phenol; 5-tridecenyl resorcinol; 5-pentadecenyl resorcinol; cardanol which is a phenol having a straight-chain unsaturated hydrocarbon group having 15 carbon atoms in a meta position; cardol which has a straight-chain unsaturated hydrocarbon group having 15 carbon atoms and a hydroxyl group in a meta position; 2-methyl cardol which is a phenol having a straight-chain unsaturated hydrocarbon group having 15 carbon atoms and a hydroxyl group in a meta position, and a methyl group in an ortho position; and the like. Among these, from the viewpoint of handleability, it is preferable to use cardanol, cardol, and 2-methyl cardol. These may be used alone or in combination of two or more thereof.

In addition, the liquid resol-type phenolic resin according to the present embodiment may be obtained by reacting a phenol compound (B) which is obtained through a reaction with the above-described phenols (A) in the presence of an acid catalyst, with aldehydes (C), in the presence of a basic catalyst, and may be obtained by reacting the above-described phenols (A) with the aldehydes (C) in the presence of a basic catalyst.

As described above, the liquid resol-type phenolic resin according to the present embodiment is not particularly limited. For example, it is possible to obtain the liquid resol-type phenolic resin by reacting a phenol compound (B) which is obtained through a reaction with the above-described phenols (A), in which the straight-chain unsaturated hydrocarbon group having equal to or more than 10 carbon atoms is bonded to at least one or more meta positions, in the presence of an acid catalyst, with aldehydes (C), in the presence of a basic catalyst. By doing this, it is possible to further improve the flexibility of the wet paper friction material. The phenols (A) themselves, in which the straight-chain unsaturated hydrocarbon group having equal to or more than 10 carbon atoms is bonded to at least one or more meta positions, show acidity, and therefore, the phenols can be reacted without adding the acid catalyst.

Here, in a case where the liquid resol-type phenolic resin according to the present embodiment is obtained by reacting the phenol compound (B) which is obtained through a reaction with the above-described phenols (A) in the presence of an acid catalyst, with the aldehydes (C) in the presence of a basic catalyst, the reaction described below is considered to proceed.

First, a carbocation is generated by adding a proton ($H^+$), which is supplied from an acid catalyst, to a carbon-carbon multiple bond of the straight-chain unsaturated hydrocarbon group having equal to or more than 10 carbon atoms in the phenols (A). Next, it is considered that a substitution reaction occurs between the generated carbocation and a benzene ring in other molecules of the phenols (A), and the phenol compound (B) is generated. It is considered that a substitution reaction occurs even between the straight-chain unsaturated hydrocarbon group which has equal to or more than 10 carbon atoms and which is bonded to the above-described other molecules of the phenols (A), and the benzene ring in other molecules of the phenols (A). It is possible to obtain the liquid resol-type phenolic resin according to the present embodiment by reacting the phenol compound (B) generated in this manner with the aldehydes (C) in the presence of a basic catalyst.

In addition, in the case of obtaining the above-described phenol compound (B), the used acid catalyst is not particularly limited, but examples thereof include organic acids such as acetic acid and oxalic acid; mineral acids such as hydrochloric acid, sulfuric acid, and phosphoric acid; diethyl sulfate; p-toluenesulfonic acid; and p-phenolsulfonic acid.

In addition, the liquid resol-type phenolic resin according to the present embodiment can also be obtained by reacting the phenols (A), in which the straight-chain unsaturated hydrocarbon group having equal to or more than 10 carbon atoms is bonded to at least one or more meta positions, with the aldehydes (C) in the presence of a basic catalyst without being subjected to the reaction in the presence of an acid catalyst. By doing this, it is possible to obtain the liquid resol-type phenolic resin which is excellent from the viewpoint of hardenability as a characteristic of the phenolic resin and is suitable for obtaining the wet paper friction material more excellent in flexibility.

In the case where the liquid resol-type phenolic resin according to the present embodiment is obtained by reacting the above-described phenols (A) and the aldehydes (C) in the presence of a basic catalyst, it is preferable that the liquid resol-type phenolic resin repeatedly include the structural unit represented by the following general formula (2). By doing this, it is possible to obtain the liquid resol-type phenolic resin which is excellent from the viewpoint of hardenability as a characteristic of the phenolic resin and is suitable for obtaining the wet paper friction material more excellent in flexibility.

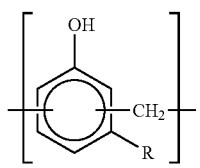

(2)

(In the formula, R represents a straight-chain unsaturated hydrocarbon group having equal to or more than 10 carbon atoms. However, a hydrogen atom which is bonded to a benzene ring having a phenolic hydroxyl group may be substituted by a substituent.)

In addition, in a case where the phenols (A) and/or the phenol compound (B) is/are reacted with the aldehydes (C) in the presence of a basic catalyst, or in a case where the phenols (A) are reacted with the aldehydes (C) in the presence of a basic catalyst, the molar ratio (C)/{(A)+(B)} of the reactant is preferably equal to or more than 0.2 and equal to or less than 1.5, and more preferably equal to or more than 0.6 and equal to or less than 1.2. By setting the molar ratio during the reaction to the above-described range, it is possible to reduce the amount of the aldehydes (C) that remain without reaction and to obtain a phenolic resin having sufficient hardenability.

In the case where the phenols (A) and/or the phenol compound (B) is/are reacted with the aldehydes (C) in the presence of a basic catalyst, or in the case where the phenols (A) are reacted with the aldehydes (C) in the presence of a basic catalyst, the used basic catalyst is not particularly limited, but examples thereof include hydroxides of alkali metals such as sodium hydroxide, lithium hydroxide, and potassium hydroxide; tertiary amines such as ammonia water or triethylamine; oxides and hydroxides of alkaline earth metals such as calcium, magnesium, and barium; and a basic substance such as sodium carbonate. These may be used alone or in combination of two or more thereof. In addition, the amount used of the basic catalyst is not particularly limited, but equal to or more than 1 part by mass and equal to or less than 50 parts by mass thereof may be used with respect to 1000 parts by weight of the phenols (A) or the phenol compound (B).

The liquid resol-type phenolic resin according to the present embodiment is characterized in that the straight-chain unsaturated hydrocarbon group having equal to or more than 10 carbon atoms is bonded to at least one or more of meta positions of all of phenol structure units, and can be obtained by reacting the above-described phenols (A) and/or the phenol compound (B) with the aldehydes (C) in the presence of a basic catalyst.

In addition, the aldehydes (C) are not particularly limited, but examples thereof include formaldehyde, acetaldehyde, butyraldehyde, propionaldehyde, terephthalic aldehyde, benzaldehyde, paraformaldehyde, and acrolein. The usage is not limited to a kind thereof and the aldehydes can be used alone or in combination of two or more thereof. In addition, it is possible to use a substance which becomes a source of the aldehydes or a solution of the aldehydes. In general, it is preferable to use an aqueous formaldehyde solution from an aspect of cost.

In addition, an organic solvent may be used for the liquid resol-type phenolic resin according to the present embodiment in order to dilute the resin. Here, the organic solvent used for diluting the resin is not particularly limited, but examples thereof include alcohol-based organic solvents such as methanol, ethanol, isopropanol, and butanol; ketone-based organic solvents such as acetone, methyl ethyl ketone, and methyl isobutyl ketone; aromatic hydrocarbon solvents such as toluene and ethylbenzene; and a mixture thereof.

It is preferable to use the liquid resol-type phenolic resin according to the present embodiment by being impregnated to a base material. The base material used herein is not particularly limited, but examples thereof include a base material in which fibers such as natural fibers, metal fibers, carbon fibers, and chemical fibers are used along or in a combination of two or more thereof.

It is preferable to use the liquid resol-type phenolic resin according to the present embodiment by being contained in the wet paper friction material. An example of a method of manufacturing the wet paper friction material containing the above-described liquid resol-type phenolic resin includes a method in which the liquid resol-type phenolic resin is impregnated into a paper base material filled with metal fibers or carbon fibers and chemical fibers, a friction adjuster such as cashet dust, diatomaceous earth, and the like, to fire and cure these. By doing this, it is possible to obtain the wet paper friction material according to the present embodiment.

<Wet Paper Friction Material>

The wet paper friction material according to the present embodiment is formed using the above-described liquid resol-type phenolic resin. By doing this, it is possible to realize the wet paper friction material which is excellent from the viewpoint of heat resistance or hardenability as a characteristic of the phenolic resin and is more excellent in flexibility.

Hereinabove, the embodiment of the present invention has been described, but the embodiment is an example of the present invention and various configurations other than the above can also be employed.

Hereinafter, an example of a referential mode is appended.
(1) A liquid resol-type phenolic resin including:
an equal to or more than 10 carbon atoms straight-chain unsaturated hydrocarbon group in at least one or more of meta positions of all of phenol skeletons.
(2) The liquid resol-type phenolic resin according to (1),
in which the liquid resol-type phenolic resin is obtained by reacting a phenol compound (B), which is obtained through a reaction with phenols (A) having the equal to or more than 10 carbon atoms straight-chain unsaturated hydrocarbon group in at least one or more of meta positions in the presence of a acid catalyst, with aldehydes (C) in the presence of a basic catalyst.
(3) The liquid resol-type phenolic resin according to (1),
in which the liquid resol-type phenolic resin is obtained by reacting the phenols (A) having the equal to or more than 10 carbon atoms straight-chain unsaturated hydrocarbon group in at least one or more of meta positions, with the aldehydes (C) in the presence of a basic catalyst.
(4) The liquid resol-type phenolic resin according to (2) or (3),
in which the phenols (A) are at least one or more phenols selected from a group consisting of cardanol, cardol, and 2-methyl cardol.
(5) The liquid resol-type phenolic resin according to any one of (1) to (4),
in which the liquid resol-type phenolic resin is used for impregnation.
(6) The liquid resol-type phenolic resin according to any one of (1) to (5), which is used for a wet paper friction material.
(7) A wet paper friction material which is formed using the liquid resol-type phenolic resin according to (6).

EXAMPLES

Hereinafter, examples of the present invention will be described in more detail. However, the present invention is not limited to the examples. In addition, "parts" and "%" which are described in the examples and comparative examples respectively indicate "parts by weight" and "wt %".

Manufacture of Liquid Resol-Type Phenolic Resin

Example 1

1000 parts of cardanol and 15 parts of p-toluenesulfonic acid were added to a reaction apparatus provided with a stirring device, a reflux condenser, and a thermometer and were reacted for an hour while being stirred and heated to raise the temperature to 140° C. 180 parts (molar ratio with the cardanol reactant=0.8) of a 37% aqueous formalin solution, 5 parts of triethylamine, and 10 parts of a 50% aqueous sodium hydroxide solution were added thereto and the mixture was reacted for 2 hours while being stirred at a temperature of 60° C. Then, 280 parts of toluene and 670 parts of methanol were added thereto when the temperature in the system reached 65° C. while performing dehydration under reduced pressure at 91 kPa, and the mixture was dissolved and cooled. By doing this, 2100 parts of a liquid resol-type phenolic resin a with a non-volatile component of 45% was obtained.

Example 2

1000 parts of cardanol, 180 parts (molar ratio with the cardanol=0.8) of a 37% aqueous formalin solution, 5 parts of triethylamine, and 10 parts of a 50% aqueous sodium hydroxide solution were added to a reaction apparatus provided with a stirring device, a reflux condenser, and a thermometer and were reacted for 2 hours while being stirred at a temperature of 60° C. Then, 280 parts of toluene and 670 parts of methanol were added thereto when the temperature in the system reached 65° C. while performing dehydration under reduced pressure at 91 kPa, and the mixture was dissolved and cooled. By doing this, 2100 parts of a liquid resol-type phenolic resin b with a non-volatile component of 45% was obtained.

Comparative Example 1

1000 parts of phenol, 740 parts (molar ratio with the phenol=1.0) of a 37% aqueous formalin solution, and 20 parts of a 50% aqueous sodium hydroxide solution were added to a reaction apparatus provided with a stirring device, a reflux condenser, and a thermometer and were reacted for 30 minutes while being stirred at a temperature of 100° C. Then, 1000 parts of methanol was added thereto when the temperature in the system reached 65° C. while performing dehydration under reduced pressure at 91 kPa, and the mixture was dissolved and cooled. By doing this, 2100 parts of a liquid resol-type phenolic resin c with a non-volatile component of 45% was obtained.

Comparative Example 2

1000 parts of phenol, 540 parts of tung oil, and 1 part of p-toluenesulfonic acid were added to a reaction apparatus provided with a stirring device, a reflux condenser, and a thermometer and were reacted for 30 minutes while being stirred and heated to raise the temperature to 60° C. 770 parts (molar ratio with the phenol=1.2) of a 37% aqueous formalin solution, 1 part of triethanolamine, and 20 parts of a 25% aqueous ammonia solution were subsequently added thereto and the mixture was reacted for 2 hours while being stirred at a temperature of 100° C. Then, 280 parts of toluene and 670 parts of methanol were added thereto when the temperature in the system reached 70° C. while performing dehydration under reduced pressure at 68 cmHg, and the mixture was dissolved and cooled. By doing this, 2100 parts of a liquid resol-type phenolic resin d with a non-volatile component of 45% was obtained.

<Evaluation of Liquid Resol-Type Phenolic Resin>

Impregnated paper was prepared using the liquid resol-type phenolic resins a to d which are obtained in the examples and the comparative examples. Commercially available filter paper (120 mm×10 mm×thickness of 1 mm) was used for the base material.

The liquid resol-type phenolic resins a to d which are obtained in the examples and the comparative examples were diluted with acetone, the above-described filter paper was impregnated in a solution of which the resin concentration was set to 30%. Then, the resultant was dried and cured for 30 minutes in an oven at a temperature of 190° C. to obtain a test piece.

(Evaluation Items)

Tensile strength: The tensile strength of the obtained test piece was measured based on JIS P 8113. The unit is in MPa. The tensile strength of the test piece prepared in the above-described method was measured under measurement conditions of room temperature, standard atmospheric pressure, and a test speed of 1 mm/min, using a precision universal testing machine AG-IS 5 kN (manufactured by Shimadzu Corporation).

Tensile break elongation: The tensile break elongation of the obtained test piece was measured based on JIS P 8113. The unit is in %. The tensile break elongation of the test piece prepared in the above-described method was measured under measurement conditions of a room temperature, an ordinary pressure, and a test speed of 1 mm/min, using the precision universal testing machine AG-IS 5 kN (manufactured by Shimadzu Corporation).

Dissolution portion of cured material in acetone: The liquid resol-type phenolic resins a to d obtained in the examples and the comparative examples were cured for 30 minutes at a temperature of 190° C. Subsequently, the resultant was crushed using a bead mill and was sieved to prepare a sample which passed through a 149 μm sieve and remained on a 63 μm sieve. About 20 Glass beads and 200 ml of acetone were put into a soxhlet flask. Cylindrical filter paper was put into an extraction tube, about 3 g of a weighed sample was put into the filter paper, and the sample was immersed in the acetone for 6 hours while refluxing the mixture by attaching and fixing a condenser to the extraction tube so as to be a state of a water bath. Then, the acetone was dried using a vacuum dryer and an extraction rate of the acetone was calculated from the weight of the remaining resultant. It is possible to determine that more curing proceeds as the amount of the acetone dissolution portion is small.

The evaluation result in relation to the above-described evaluation items is shown in the following Table 1.

TABLE 1

|  | Example 1 | Example 2 | Comparative Example 1 | Comparative Example 2 |
| --- | --- | --- | --- | --- |
| Liquid resol-type phenolic resin | a | b | c | d |
| Phenols (A) or phenol compound (B) | Cardanol/ after acid catalyst reaction | Cardanol | Unmodified phenol | Tung oil-modified phenol |

TABLE 1-continued

| | Example 1 | Example 2 | Comparative Example 1 | Comparative Example 2 |
|---|---|---|---|---|
| Tensile strength (MPa) | 12.5 | 12.0 | 11.9 | 11.2 |
| Tensile break elongation (%) | 6.6 | 5.4 | 2.2 | 4.3 |
| Dissolution portion of cured material in acetone (%) | 0.6 | 0.6 | 0.5 | 2.5 |

It can be seen that the cured materials of the phenolic resins a and b obtained in Examples 1 and 2 are excellent in hardenability since the amount of the acetone dissolution portion is small and are excellent in flexibility since the tensile break elongation is great. In reality, in a case of manufacturing a wet paper friction material using the phenolic resins a and b described in the examples, it was possible to obtain the wet paper friction material excellent in flexibility.

The phenolic resin c obtained in Comparative Example 1 is an unmodified liquid resol-type phenolic resin which is obtained from phenol and formaldehyde, and the phenolic resin d obtained in Comparative Example 2 is a liquid resol-type phenolic resin which is modified by tung oil as drying oil. The phenolic resin d of Comparative Example 2 had greater tensile break elongation and was more excellent in flexibility compared to the phenolic resin c of the Comparative Example 1. However, the phenolic resin d thereof has poorer flexibility compared to the phenolic resins a and b of Examples 1 and 2. In addition, the phenolic resin d of the Comparative Example 2 had poor hardenability since the amount of the acetone dissolution portion was large. Moreover, the phenolic resin d thereof had poorer tensile strength compared to the phenolic resins a and b of Examples 1 and 2.

It is possible to obtain a molded product which has characteristics of the phenolic resin excellent in hardenability and the like and is excellent in flexibility using the liquid resol-type phenolic resin of the present invention. In particular, the liquid resol-type phenolic resin of the present invention can be favorably used for friction materials.

Priority is claimed on Japanese Patent Application No. 2012-123992, filed on May 31, 2012, the whole disclosure of which is incorporated herein by reference.

The invention claimed is:

1. A liquid resol-type phenolic resin, wherein a straight-chain unsaturated hydrocarbon group having equal to or more than 10 carbon atoms is bonded to at least one or more of meta positions of all of phenol structure units.

2. The liquid resol-type phenolic resin according to claim 1, wherein the liquid resol-type phenolic resin is obtained through a reaction with phenols (A) in which the straight-chain unsaturated hydrocarbon group having equal to or more than 10 carbon atoms is bonded to at least one or more of the meta positions.

3. The liquid resol-type phenolic resin according to claim 2, wherein the phenols (A) include a structure represented by the following general formula (1),

(1)

(In the formula, R represents a straight-chain unsaturated hydrocarbon group having equal to or more than 10 carbon atoms, however, a hydrogen atom which is bonded to a benzene ring having a phenolic hydroxyl group may be substituted by a substituent).

4. The liquid resol-type phenolic resin according to claim 1, wherein the liquid resol-type phenolic resin is obtained by reacting a phenol compound (B) which is obtained through a reaction with the phenols (A) in the presence of an acid catalyst, with aldehydes (C), in the presence of a basic catalyst.

5. The liquid resol-type phenolic resin according to claim 1, wherein the liquid resol-type phenolic resin is obtained by reacting the phenols (A) with the aldehydes (C) in the presence of a basic catalyst.

6. The liquid resol-type phenolic resin according to claim 5, wherein the liquid resol-type phenolic resin repeatedly includes a structural unit represented by the following general formula (2),

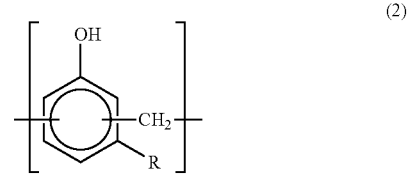

(2)

(In the formula, R represents a straight-chain unsaturated hydrocarbon group having equal to or more than 10 carbon atoms, however, a hydrogen atom which is bonded to a benzene ring having a phenolic hydroxyl group may be substituted by a substituent).

7. The liquid resol-type phenolic resin according to claim 2, wherein the phenols (A) are at least one or more phenols selected from a group consisting of cardanol, cardol, and 2-methyl cardol.

8. The liquid resol-type phenolic resin according to claim 1, which is used by being impregnated to a base material.

9. A wet paper friction material which is formed using the liquid resol-type phenolic resin according to claim 1.

* * * * *